(12) United States Patent
Van Zuylen et al.

(10) Patent No.: US 9,173,710 B2
(45) Date of Patent: Nov. 3, 2015

(54) PACKAGING SYSTEM AND METHOD FOR PACKAGING FIBERS

(75) Inventors: Jeffrey Van Zuylen, Mississauga (CA); Richard Grant Dobrowney, Petersburg (CA)

(73) Assignee: ACCUTECH MEDICAL TECHNOLOGIES INC., Cambridge, Ontario (CA)

( * ) Notice: Subject to any disclaimer, the term of this patent is extended or adjusted under 35 U.S.C. 154(b) by 449 days.

(21) Appl. No.: 12/904,611

(22) Filed: Oct. 14, 2010

(65) Prior Publication Data

US 2011/0085775 A1     Apr. 14, 2011

Related U.S. Application Data

(60) Provisional application No. 61/251,473, filed on Oct. 14, 2009.

(51) Int. Cl.
| *A61B 19/02* | (2006.01) |
| *A61B 18/22* | (2006.01) |
| *G02B 6/44* | (2006.01) |
| *A61N 5/06* | (2006.01) |
| *B65D 85/04* | (2006.01) |

(52) U.S. Cl.
CPC ............ *A61B 19/026* (2013.01); *G02B 6/4457* (2013.01); *A61B 19/0256* (2013.01); *A61B 2018/2205* (2013.01); *A61B 2019/0213* (2013.01); *A61B 2019/0267* (2013.01); *A61N 2005/063* (2013.01); *B65D 85/04* (2013.01)

(58) Field of Classification Search
None
See application file for complete search history.

(56) References Cited

U.S. PATENT DOCUMENTS

| 3,185,299 | A | | 5/1965 | Trainer | |
| 3,301,393 | A | | 1/1967 | Regan, Jr. et al. | |
| 3,352,412 | A | | 11/1967 | Draving et al. | |
| 3,495,703 | A | | 2/1970 | Calabrese | |
| 3,727,858 | A | | 4/1973 | Cornwell et al. | |
| 4,685,636 | A | | 8/1987 | Eaton | |
| 4,846,343 | A | * | 7/1989 | Rupert | B65D 85/04 206/303 |
| 4,974,789 | A | | 12/1990 | Milburn | |
| 5,263,585 | A | * | 11/1993 | Lawhon et al. | B65D 85/04 206/388 |
| 5,344,011 | A | | 9/1994 | DiBernardo et al. | |
| 6,053,313 | A | | 4/2000 | Farrell et al. | |
| 6,349,893 | B1 | | 2/2002 | Daoud | |
| 6,650,821 | B1 | * | 11/2003 | Koyano et al. | 385/136 |
| 6,745,971 | B1 | | 6/2004 | Renzoni | |
| 7,266,283 | B2 | | 9/2007 | Kline et al. | |
| 2002/0191938 | A1 | * | 12/2002 | Sheetz et al. | G02B 6/4453 385/135 |
| 2011/0116757 | A1 | * | 5/2011 | Vanmeulen et al. | 385/135 |

* cited by examiner

*Primary Examiner* — Michelle R Connelly
*Assistant Examiner* — John M Bedtelyon
(74) *Attorney, Agent, or Firm* — Gowling Lafleur Henderson LLP; Neil Henderson

(57) ABSTRACT

A packaging system and method for use with a fiber, and in particular, an optical fiber of the type typically used for surgical procedures, in order to protect the fiber during storage and shipping and also allow the fiber to be easily dispensed in a controlled manner by an end user.

21 Claims, 16 Drawing Sheets

PACKAGING SYSTEM AND METHOD FOR PACKAGING FIBERS

RELATED APPLICATIONS

This application claims priority to U.S. Provisional Application No. 61/251,473 filed Oct. 14, 2009, the content of which is herein incorporated by reference.

FIELD

The present application relates to the field of packaging and, more particularly, to the packaging of surgical or optical fibers for the medical industry.

BACKGROUND

Optical fibers have been used for many years in the medical field for surgical applications using high power lasers. The optical fibers are used primarily in their basic form, consisting of a core, cladding, primary coating (buffer) and a jacket. As such they do not contain much in the way of strengthening or protective layers which are typically added to the optical fiber when used as cables in telecom applications for example. The core and cladding are typically made with silica glass with cores ranging in diameter from 200 um (small core) to 1000 um (large core), thus the optical fibers, consisting of thin strands of glass, are easily damaged or broken with handling and shipping. The optical fibers are also typically attached at one end (proximal end) to a large and relatively heavy (compared to small core optical fibers) metal ferrule assembly (connector) which is used to facilitate connection of the optical fiber to the laser system. The complete assembly, the optical fiber and the connector are known generally as a surgical fiber. Thus there is a strong need for suitable packaging in order to protect the surgical fiber until it is used for the clinical procedure, helping to ensure safety and efficacy.

Packaging of surgical fibers presents many unique requirements including but not limited to the following. Small core optical fibers are extremely fragile whereas large core optical fibers are extremely stiff and can become quite dangerous when wound tightly under tension. The glass of the optical fiber is typically exposed by removing the jacket or jacket and buffer for a number of millimeters at the application end (distal end) and the glass core/cladding is cleaved, presenting a sharp edge around the perimeter which is easily chipped or damaged. Optical fibers are typically provided in short lengths on the order of 3 meters. The metal ferrule assembly, if not secured, could easily break the optical fiber during typical shipping conditions. The surgical fibers are generally supplied sterile therefore packaging must be able to withstand sterilization cycles, such as Ethylene Oxide or Steam sterilization, which can present extremes in temperature and pressure. As well the packaging must be able to maintain sterility and product functionality over extremes in temperature, humidity, vibration and shock which are typically encountered when shipped throughout the world. Surgical fibers can be sold as single use devices and the device and packaging discarded, thus packaging cost is a consideration. Surgical fibers must be easily dispensed into the sterile field within the operating room.

Numerous designs are currently available, the most common being a single plane card, either plastic or cardboard which is die cut and has numerous tabs, raised at angles from the card, which allow the optical fibers and connectors to be held onto the card. The optical fibers are typically wound around a number of these tabs and opposing tabs hold the connector. These designs exhibit a number of limitations such as the creation of pinch points, which can damage the jacket of the optical fiber or fracture the glass, and difficulty in removing the optical fibers by the end user as the optical fiber must be removed one tab at a time or in its entirety removing the wound optical fiber as one unit. Once the removal process has started, it is difficult to stop as the optical fiber will start to disengage from the tabs by itself. A multitude of tabs is required in order to support optical fibers of different sizes on a single card design as the large optical fibers are very rigid and small optical fibers are very flexible. Holding large core optical fibers is more difficult as under tight diameters, the optical fiber exhibits a lot of force on the tabs, with a tendency for the optical fiber to spring off the card. Also, it is difficult to control the exact resting location of the cleaved distal end of the optical fiber on the card as surgical fibers can vary slightly in length during production resulting in the cleaved distal end falling in unsuitable locations, in the round of a corner for example, with the end of the optical fiber unsecure or just under a tab for example, where the end of the optical fiber can easily pop out during transit. This exposed cleaved glass end is thus easily damaged on these tabs or presents a risk to the primary sterile barrier, typically a tyvek/plastic film pouch, which could be punctured by the sharp edge of the cleaved distal tip, should it spring loose of a tab.

Most current designs are not capable of supporting adequately multiple sizes (diameters) of surgical fibers due to the significant variance in mechanical properties. Large core optical fibers are very rigid while small core optical fibers are flexible. Bending large core optical fibers into a small radius (<0.5 meters) requires a large amount of force. Small core optical fibers can bend into a very small radius (a few cm) and require very little force. Both optical fibers, if not held securely will tend to come loose easily during transport. Large core optical fiber holders require a great deal of rigidity in order to counteract the forces exerted by the optical fiber when bent. Small core optical fibers require the optical fiber to be wound tightly on the holder, requiring the holder to be pliable in order to avoid pressure points on the optical fiber. These two requirements conflict with each other, thus current designs do not provide suitable packaging for the optical fibers.

SUMMARY

According to one aspect herein, there is provided a packaging system that includes a storage and dispensing tray for use with an optical fiber typically used for surgical applications with high power lasers. The packaging system is composed of a rigid tray which fully encases the optical fiber in a circular trough protecting it during storage and transport. The tray provides a provision for dispensing the optical fiber in a controlled manner. The tray also holds a connector, which is typically mounted on the proximal end of the optical fiber, in a fixed position with a provision to easily remove the connector when dispending the optical fiber. In order to further protect the optical fiber while being dispensed a tip protector is placed on the distal end of the optical fiber. Provisions to support sterilization are built in to the tray.

According to another aspect herein, there is provided a packaging system for storing and dispensing fiber comprising opposing circular troughs which connect together to create a cavity (annular area) for containing the fiber and at least one exit port. Typically, the fiber will be fully encased other than the exit port. The fiber can be of various diameters and may be an optical fiber or a surgical fiber or the like.

Typically, the packaging system will comprise a lid and a base wherein one opposing circular trough will be provided by the lid and another provided by the base.

The base and lid (and similarly, the opposing troughs) may be configured such that they can be manufactured separately and then connected or separated from each other for loading or reloading the fiber. In a particular case, the base and the lid may be press fitted together by a press-fit system, for example using dimples/extensions/tabs which fit inside each other or opposing press-fit troughs or recesses or the like which fit together to connect the base and lid. In a particular case, the press-fit troughs may be annular.

The fiber is coiled inside the opposing circular troughs and is intended to be dispensed at will such that a portion may be drawn out and then further portions may be later drawn out. For example, in a medical context, it may be convenient to draw out a portion of the fiber for connection purposes or the like and then subsequently drawing out the remainder for the actual procedure.

In some cases, the packaging system may be used for a fiber having a connector (sometimes referred to as a surgical fiber). In this case, the packaging system may further comprise a connector well. In this case, finger wells may be provide adjacent to connector well to allow a user to grasp the connector. Further, the connector well may further contain connector grips to hold the connector in place in the packaging system. In a particular case, the connector grips may hold a strain relief portion of the connector.

In some cases, it may be necessary for the packaging system to have ventilation, for example, in medical environments where the fiber needs to be sterilized by being subject to a gas or steam treatment or the like. In this case, the packaging system may include a venting system that allows gas circulation within the cavity formed by the opposing troughs. The venting system may comprise tracks built into the lid or base allowing gas flow into the cavity. For example, the opposing circular troughs may be vented from the top side, the bottom side, an inner wall, an outer wall or some combination thereof. In a particular case, the vents may be semicircular troughs in the base or the lid, or alternating between the base and the lid, or in both.

Further, the press-fit system or structural elements of the packaging system may also be vented or may include a vent channel to help prevent the opposing troughs from separating under pressure or vacuum typically encountered when being sterilized. In some cases, the vents or vent channels may be in communication with a hole or holes, for example the hole may be die punched into a dimple of the press-fit system.

In a further particular case, the outer wall of the troughs may be angled away from the exit port. Further, the outer wall of the trough in the base and the lid may be angled away from the seam created between the base and the lid. In a further particular case, the inner wall of the opposing circular troughs may be the inner lid trough. The configuration of the opposing troughs is intended to allow the remaining (i.e. revolving) fiber to pass above or below the exiting fiber while dispensing.

In a particular case, the bottom of the inner lid trough located towards the inner wall of the opposing troughs in the lid may be configured such that it is not in contact with the bottom of the circular trough in the base. This facilitates a situation wherein the mating of the base to the lid does not create a seam which can be contacted by the fiber, particularly as the fiber is drawn out of the packaging system.

In a still further particular case, the exit port consists of a three sided exit trough, which does not contain any sharp edges and/or which serves to isolate the fiber from any sharp edges. In a particular case, the angle of the exit port may be tangent to the diameter of the inner wall of the trough on which the exit port is provided. The exit port may be located between the upper (lid) and lower (base) trough.

The packaging system is intended to be configured such that the orientation of the coiled fiber, in particular the position of the end of the fiber, does not affect the fiber's ability to be dispensed.

The packaging system may be configured such that it is suitable for single use medical devices or for reusable medical devices.

The various aspects of the packaging system herein may comprise vacuum formed plastic material or alternatively high temperature plastic. In particular cases, the packaging system may be formed of a rigid material and may be formed such that the overall shape includes a chevron shape in order to better match the shape of sterility maintaining barriers generally used in conjunction with the packaging system. The packaging system may further be provided with rounded corners to avoid risk of damage to other packaging systems or gloves or the like that may be in use in a sterile medical environment. The packaging system may further include an external semicircular trough that circumnavigates the outer perimeter which may serve to effectively reduce the sharp edge of the perimeter and may add rigidity and may serve as a means of interconnecting various vents.

According to another aspect herein, there is provided a fiber protector for protecting the end of a fiber during removal from packaging or insertion/connection to devices and handling. In a particular case, the fiber protector comprises a sleeve configured to cover an end of an optical fiber. The provision of protection is particularly important for fibers provided with a cleaved end. The sleeve may be shorter or longer depending on the forces that may be applied to the fiber during handling. In some cases the inner profile of the sleeve may be rippled. In this case, the surface contact with the fiber is reduced and allows for gas flow within the sleeve. In further cases, the overall cross section of the sleeve may be an oval and may become more circular when placed on a fiber. The sleeve may be made of lubricious material and may have a bright safety related color.

According to another aspect herein, there is provided a fiber packaging system including: a top portion comprising a top trough, wherein the top trough forms an annular shape in the top portion; a bottom portion comprising a bottom trough, wherein the bottom trough forms an annular shape on the bottom portion and is configured to oppose and engage with the top trough when the top portion and bottom portion are engaged in order to form an annular area for supporting a fiber; and an exit port provided to at least one of the top portion and bottom portion to allow the fiber to exit from the annular area.

In a particular case, the top portion and bottom portion may be configured such that the fiber is substantially fully encased.

In another particular case, the opposing top and bottom troughs may be configured to be separable from each other.

In a further particular case, the opposing annular top and bottom troughs may be substantially circular in shape.

In yet another particular case, at least one of the top portion and bottom portion may further include a connector well to receive a connector provided to an end of the fiber. In this case, the connector well may include grips to hold the connector at a strain relief location of the connector.

In still yet another particular case, the top portion and the bottom portion may be press fitted together. In this case, the press fitting may include interlocking press fit elements provided to the top portion and the bottom portion. In this case, the press fit elements may be vented.

In still another particular case, the annular area may be vented.

In yet another particular case, an outer wall of the top and bottom troughs may be angled away from the exit port and/or from any seams.

In another particular case, the top trough may further include a top inner trough configured to engage with an inner wall of the bottom trough and drive the fiber toward the bottom of the bottom trough in order to prevent contact with seams between inner walls of the top and bottom troughs. In this case, the top inner trough may be configured such that it does not extend to the bottom of the bottom trough.

In still yet another particular case, the mating of the top trough to the bottom trough may be configured to minimize contact by the fiber with seams created by the mating.

In yet another particular case, the exit port may be formed as a three sided trough that is configured to isolate the fiber from sharp edges as it exits the annular area.

In another particular case, the exit port may be arranged tangent to the diameter of an inner wall of the annular area.

According to another aspect herein, there is provided a method of packaging a surgical fiber comprising: coiling the fiber within a bottom trough in a bottom portion of a package; press fitting a top trough of a top portion of the package into the bottom trough; and maintaining an end of the fiber in an exit port of at least the top or bottom portion of the package.

In a particular case, the method may further include: placing the package into a pouch; and filling the pouch with a sterilizing substance that enters the package via the exit port and vent holes provided in the package.

According to yet another aspect herein, there is provided a method of dispensing a surgical fiber from a package in which the fiber is coiled in an annular area in the package, the method including: grasping an end of the fiber; and pulling the fiber out of an exit port of the packaging such that fiber remaining coiled revolves within the annular area of the package.

Other aspects and features will become apparent to those ordinarily skilled in the art upon review of the following description of specific embodiments in conjunction with the accompanying figures.

BRIEF DESCRIPTION OF THE DRAWINGS

Embodiments will now be described, by way of example only, with reference to the attached Figures, wherein.

DETAILED DESCRIPTION

Figure 1:
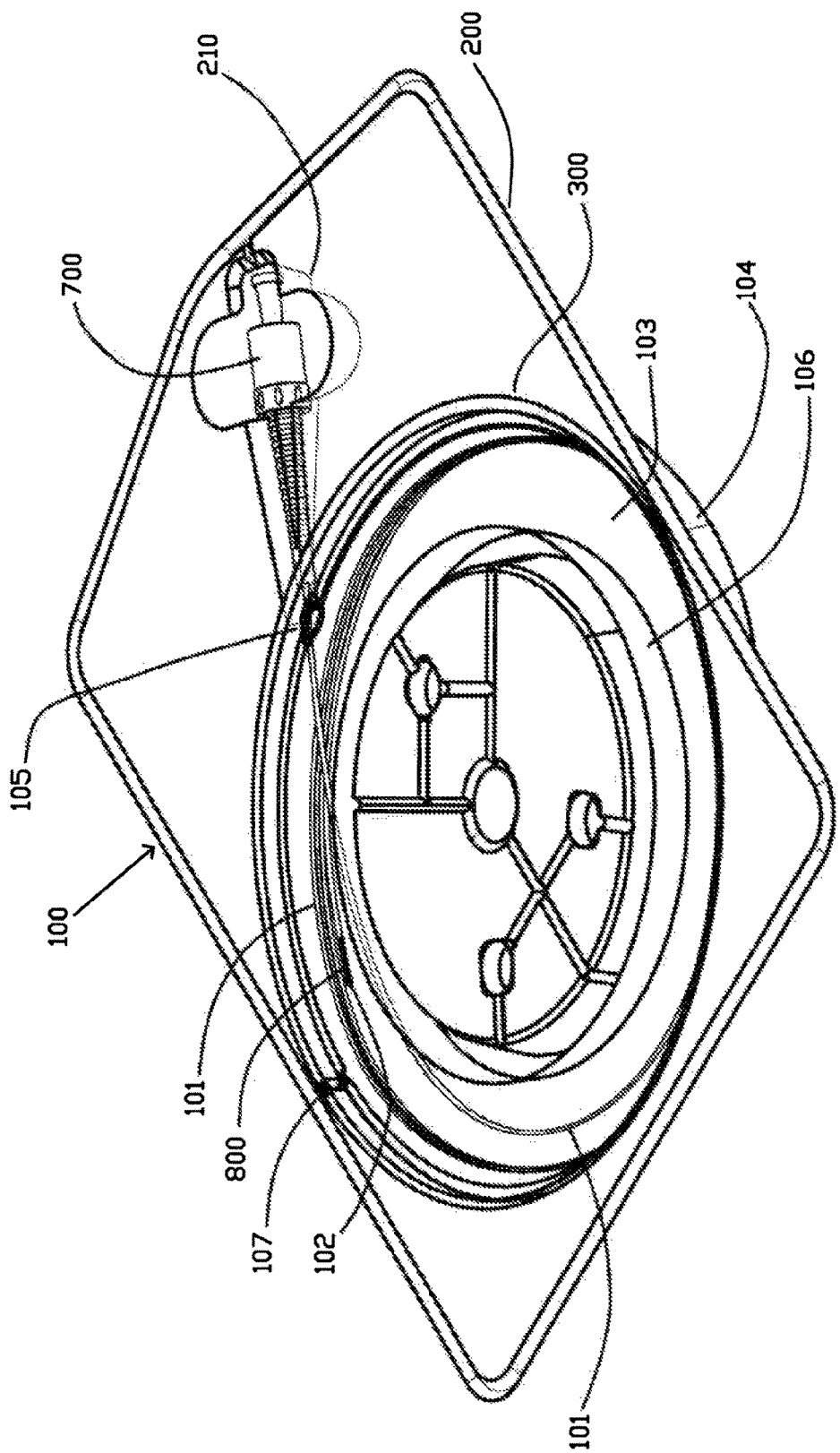
FIG. 1 shows a perspective view of a packaging system together with a surgical fiber.

It will be appreciated that for simplicity and clarity of illustration, where considered appropriate, reference numerals may be repeated among the figures to indicate corresponding or analogous elements or steps. In addition, numerous specific details are set forth in order to provide a thorough understanding of the exemplary embodiments described herein. However, it will be understood by those of ordinary skill in the art that the embodiments described herein may be practiced without these specific details. In other instances, well-known methods, procedures and components have not been described in detail so as not to obscure the embodiments described herein. Furthermore, this description is not to be considered as limiting the scope of the application in any way, but rather as merely describing the implementation of the various embodiments described herein.

Generally, the present application provides a packaging system and method for packaging fibers.

FIG. 1 shows an embodiment of a packaging system 100. The packaging system 100 stores and dispenses an optical fiber assembly (typically of the type used in surgical applications, and generally referred to as a surgical fiber) consisting of a short length of optical fiber 101 and a connector 700. The packaging system 100 consists of a base 200 (sometimes referred to as a bottom portion) and a lid 300 (sometimes referred to as a top portion), which, in this embodiment, are press-fitted together. This press-fitting allows the surgical fiber to be loaded into the tray during manufacture or reprocessing and then encased by covering the base 200 with the lid 300. Further, in this embodiment, a distal end of the surgical fiber 102 is covered with a tip protector 800.

The packaging system 100 described in this embodiment incorporates two opposing troughs 103, 104, one on the base and one on the lid, that form an annular shape on each of the base and lid and, when engaged, form an annular area for storing the fiber. In this embodiment, the annular shape is substantially circular. The troughs 103, 104 are configured such that the force exerted by the optical fiber is intended to be evenly distributed throughout the entire length of the optical fiber on to the outer wall of the troughs 103, 104. This is intended to minimize pressure points that can damage the optical fiber. This configuration is suitable for various sizes of optical fibers, provided the diameter of the trough is small enough that the optical fiber exerts force in an outward direction when bent to fit in the trough. While the outward force is typically desirable it is not required. To dispense the surgical fiber, the optical fiber is pulled from the trough through the exit port 105. The optical fiber will slide over the surface rotating on the outer wall of the trough. As the optical fiber is being dispensed it will tend to pull towards the middle of the trough. For this reason the opposing troughs have an inner wall 106 created to prevent the optical fiber from twisting over itself. This is typically of more importance for small core optical fibers as they are generally more flexible than large core optical fibers.

The circular trough design is capable of supporting adequately multiple sizes (diameters) of optical fibers which have a significant variance in mechanical properties. Large core optical fibers are more rigid while small core optical fibers are more flexible. Bending large core optical fibers into a small radius (<0.5 meters) requires a large amount of force. Small core optical fibers can bend into a very small radius (a few cm) and require very little force. In the current design, a single trough diameter is intended to be capable of handling a range of optical fiber diameters from small core to large core. In some embodiments, the trough design provides a great deal of rigidity in order to counteract the forces exerted by the large core optical fibers. It can also provide small core optical fibers a rigid barrier to protect them and eliminate any pressure points on the optical fiber itself. During transport the fully encased design holds the optical fibers securely in place.

Figure 2A:
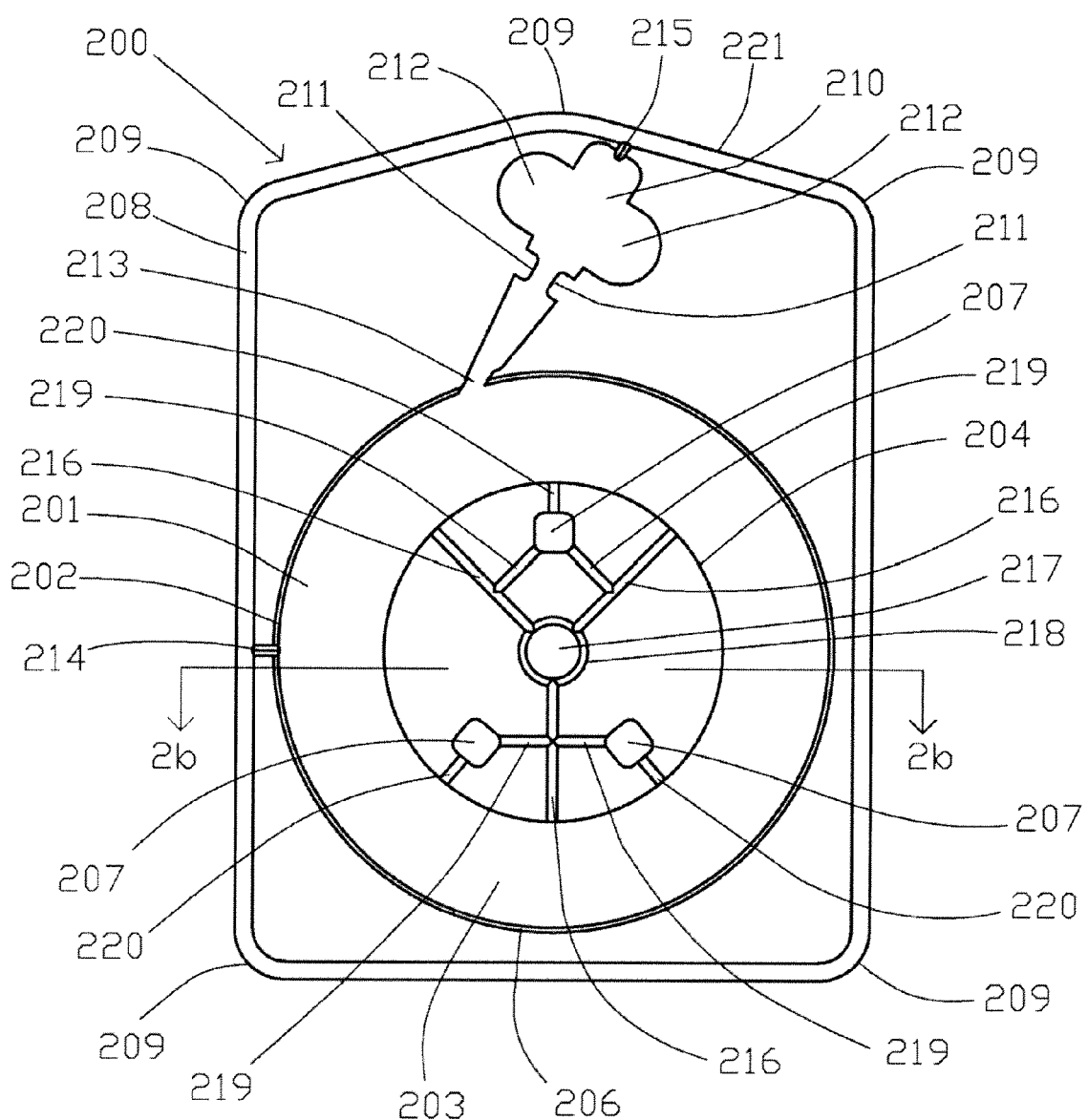
FIG. 2a shows a top view of a base of the packaging system.
Figure 2B:
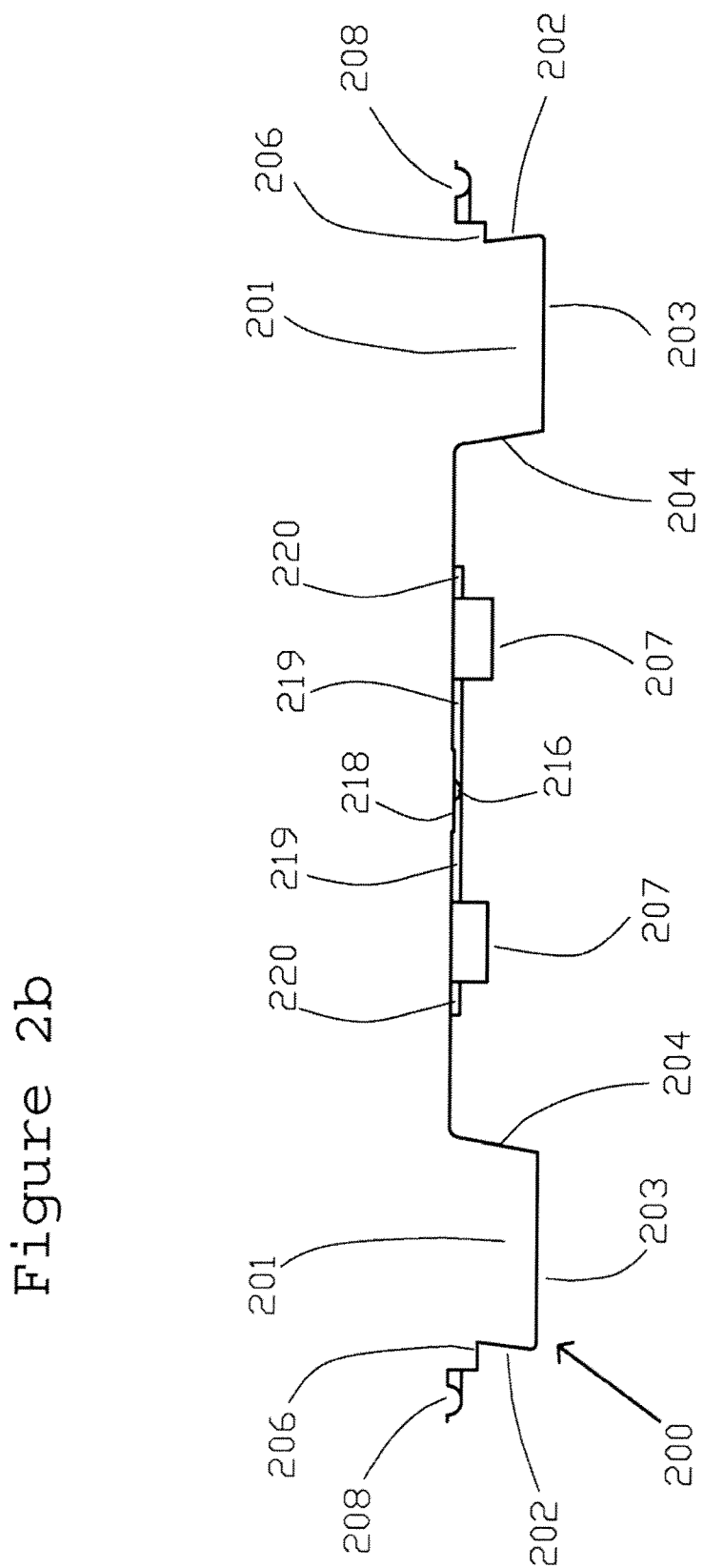
FIG. 2b shows a cross sectional view of the base.
Figure 2C:
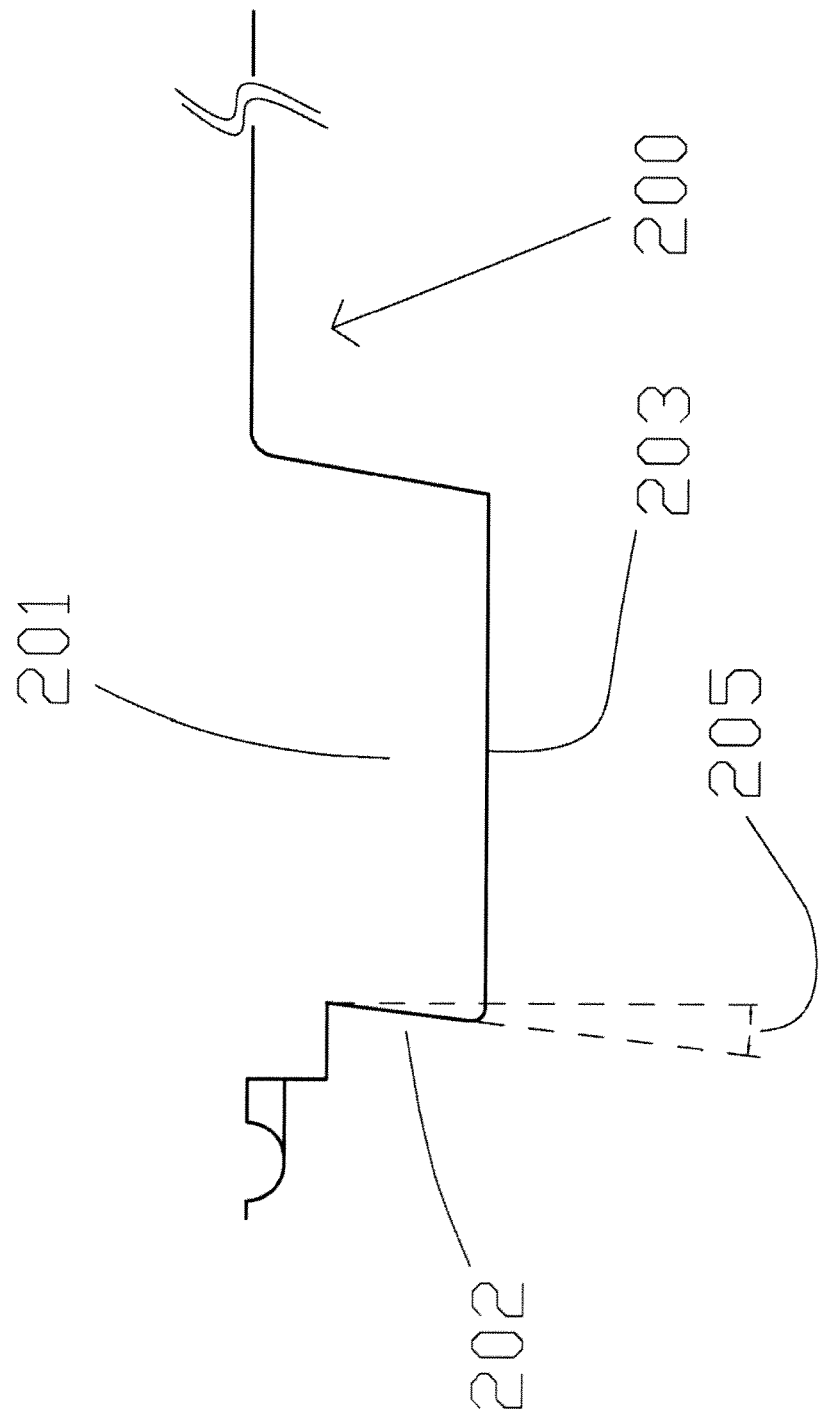
FIG. 2c shows a negative angle of the outer wall of a trough of the base.

The base 200 contains one of the opposing circular troughs as illustrated in FIGS. 2(a)-(b). The base trough 201 consists of an outer wall 202, bottom 203 and inner wall 204. In order to ensure the optical fiber is dispensed in an orderly fashion and held in position during transport a negative angle 205 is created in the outer wall 202 of the base trough as illustrated in FIG. 2(c). This angle tends to keep the optical fiber towards the bottom 203 of the base trough. This is important in order to keep the distal end of the optical fiber away from the exit port 105 when the optical fiber is being dispensed. The distal end of the optical fiber 102 could become caught in the exit port, or the cleaved end become damaged should the tip "snap" into the exit port while dispensing.

Figure 3A:
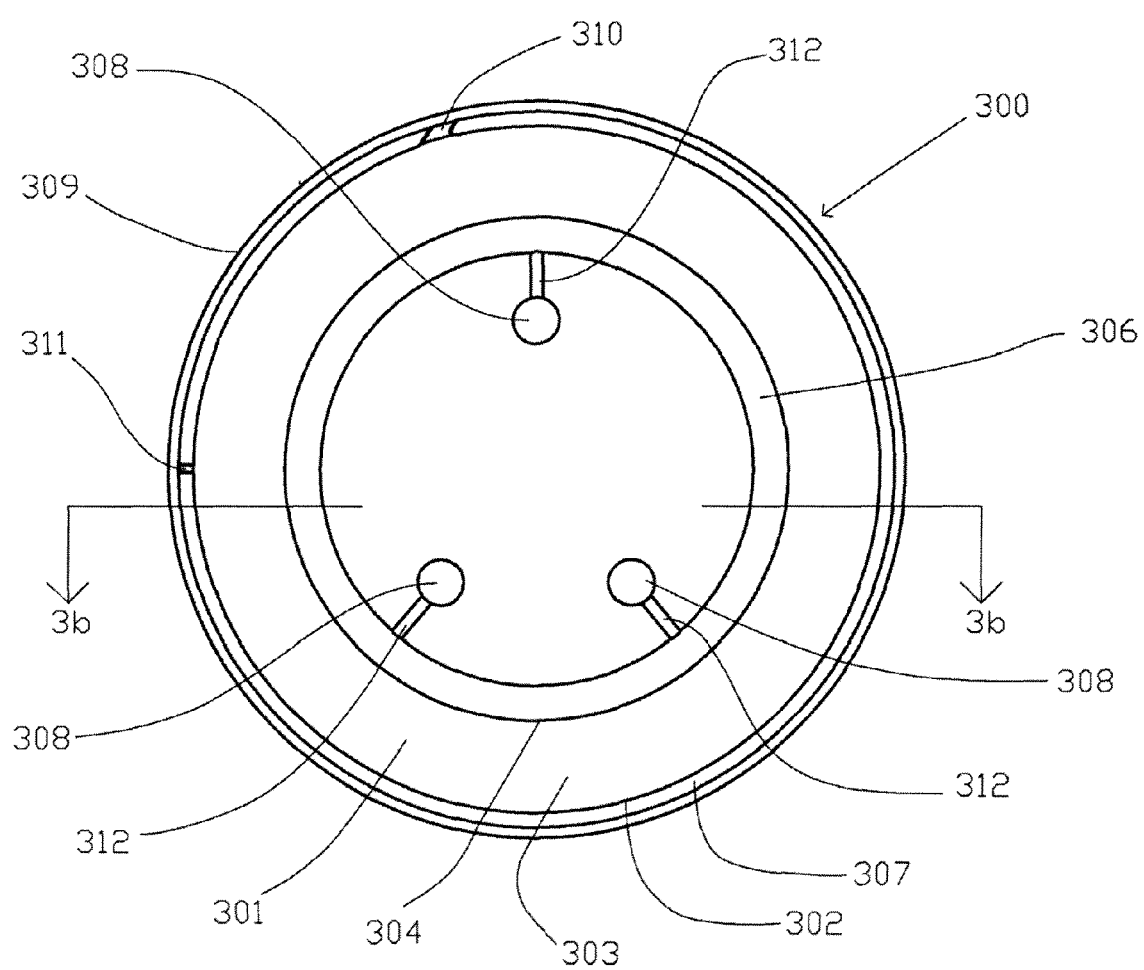
FIG. 3a shows a top view of a lid of the packaging system.
Figure 3B:
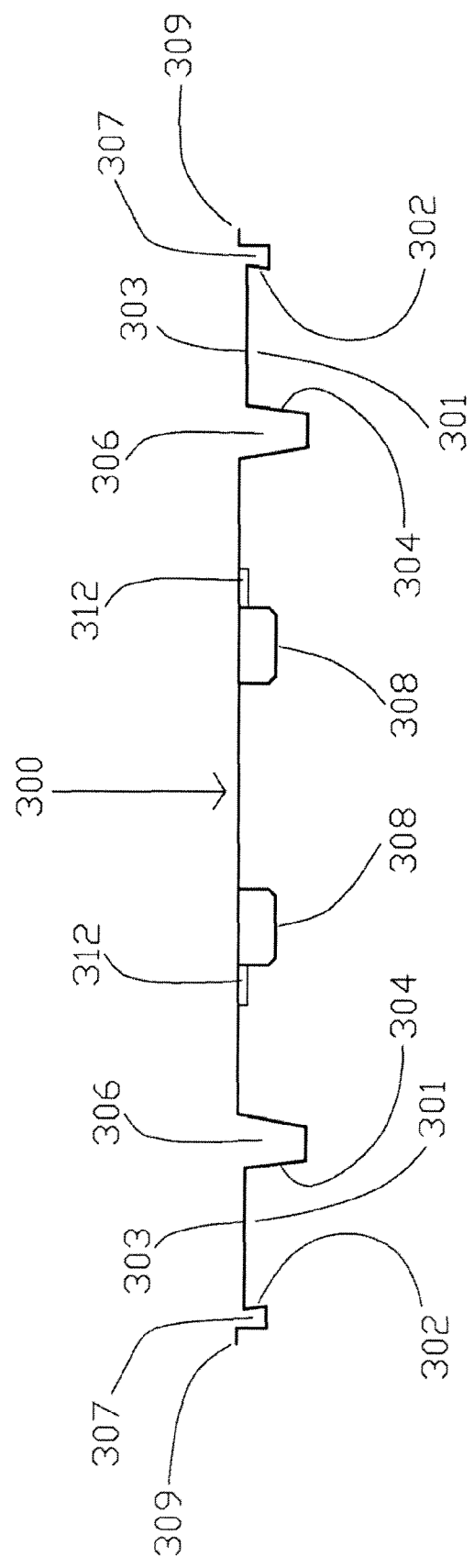
FIG. 3b shows a cross sectional view of the lid.
Figure 3C:
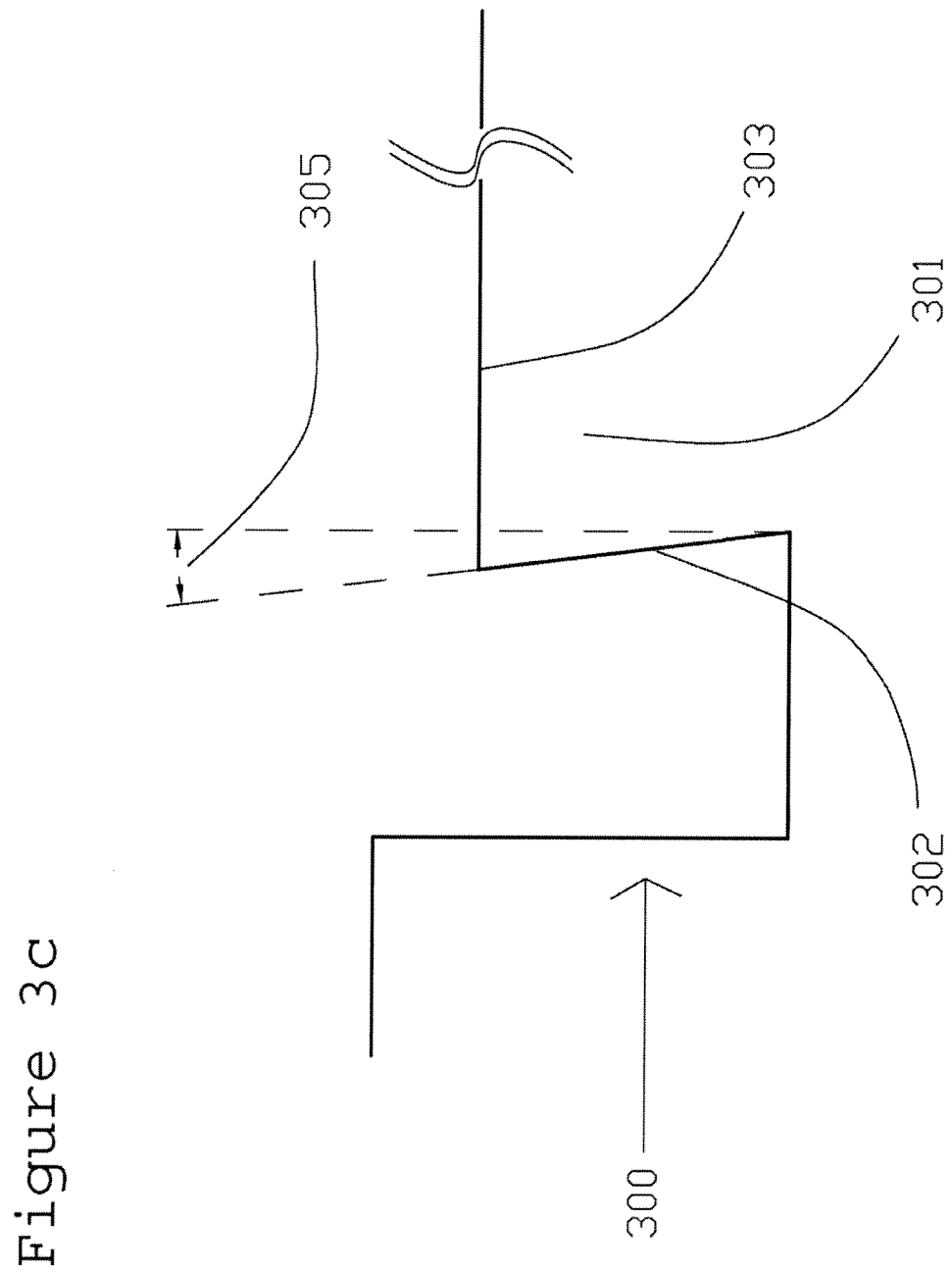
FIG. 3c shows a negative angle of the outer wall of a trough of the lid.
Figure 4A:
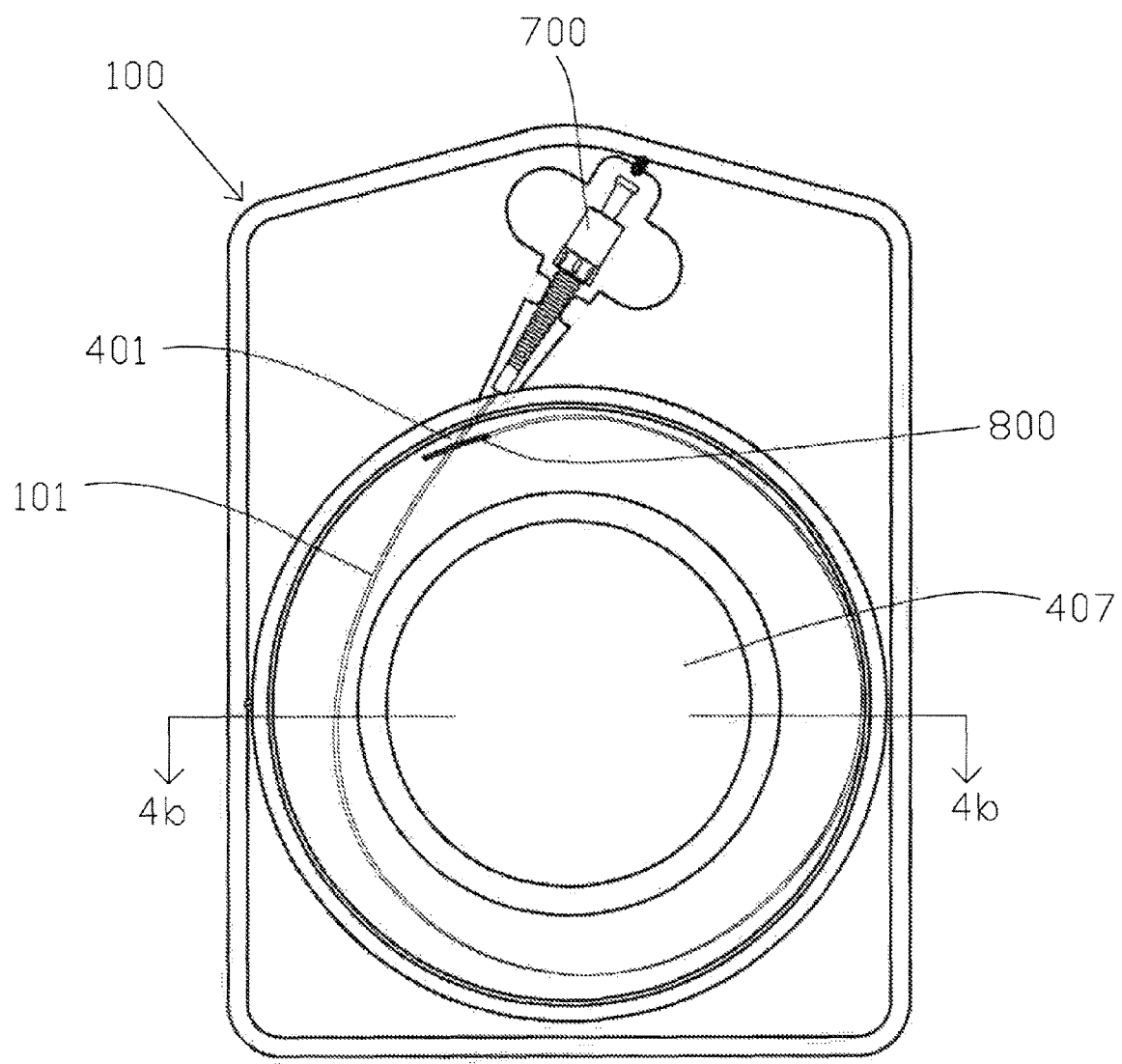
FIG. 4a shows a top view of the assembled packaging system together with the surgical fiber.
Figure 4B:
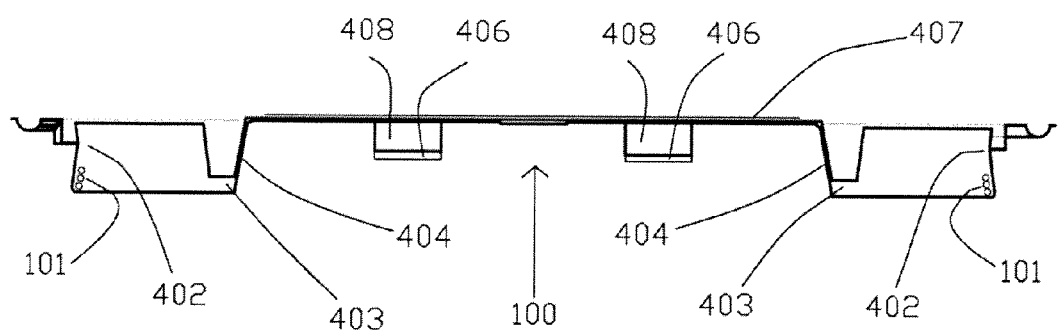
FIG. 4b shows a cross sectional view of the assembled packaging system.
Figure 4C:
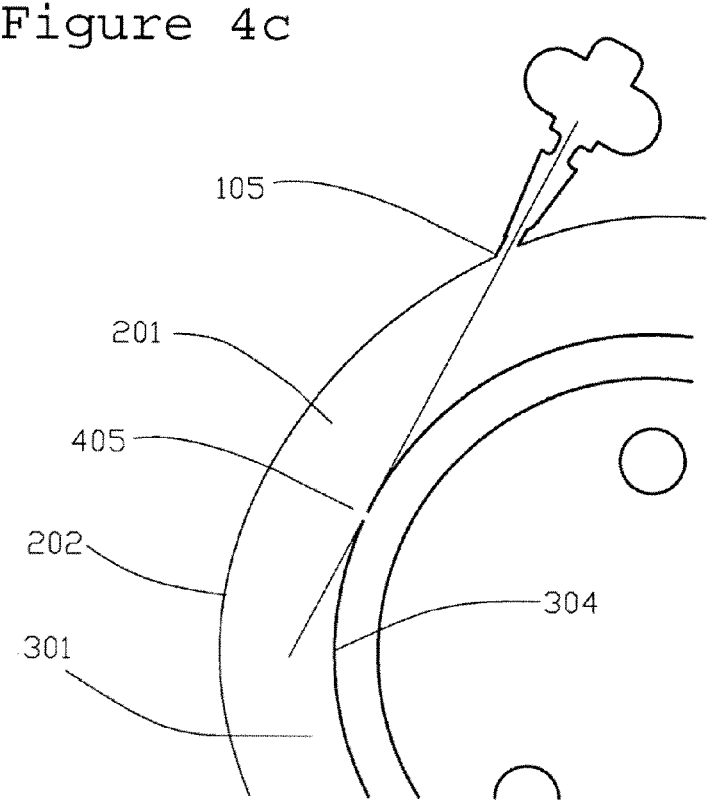
FIG. 4c illustrates that an angle of the exit port is tangent to an inner wall of an opposing circular trough.

The lid 300 contains the other opposing circular trough as illustrated in FIGS. 3(a)-(b). The lid trough 301 consists of an outer wall 302, top 303 and inner wall 304. Without the opposing circular trough it is possible that the optical fiber binds while dispensing preventing the optical fiber from exiting the packaging system 100. This can occur if the distal end of the optical fiber overlaps other optical fibers in the coil. In this case the end of the optical fiber will be drawn up to the exit port 105 when dispensing, crossing over the exiting optical fiber. This cross point 401 represents a location that can cause the optical fiber 101 to bind and lock up as illustrated in FIG. 4(a). Thus the lid trough provides space for the distal end of the optical fiber to cross over the exiting optical fiber. The lid trough 301 also contains a negative angle 305 as illustrated in FIG. 3(c) in the outer wall 302 of the trough to help direct the end of the optical fiber towards the top 303 of the lid, keeping the distal end of the optical fiber away from the exit port while dispensing. The two opposing negative angles 205 and 305 also aid in keeping the distal end of the optical fiber away from the seam 402 connecting the lid to the base as illustrated in FIG. 4(b), which presents a possible "pinch point" where the optical fiber 101 could get caught.

Figure 5A:
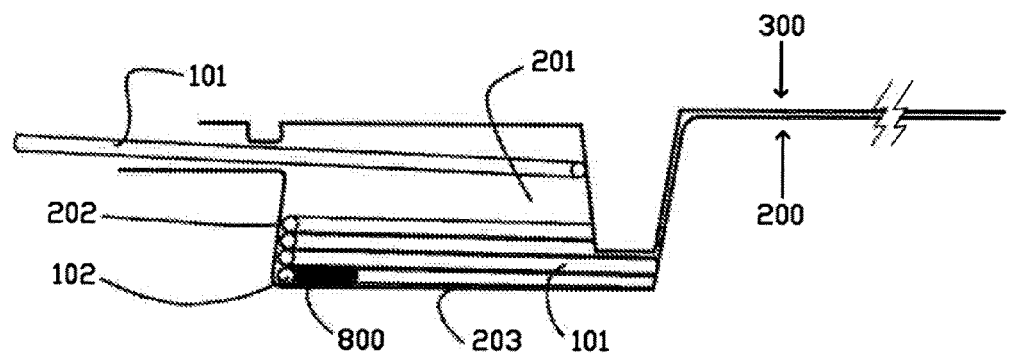
FIG. 5a shows the surgical fiber being guided in the base trough.
Figure 5B:
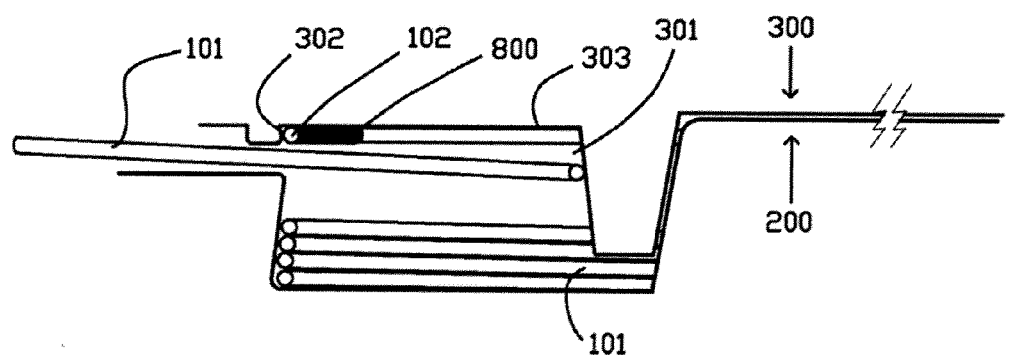
FIG. 5b shows the surgical fiber being guided in the lid trough.

For clarity, when being dispensed the distal end of the surgical fiber 102 will ideally track in the corner created by the bottom 203 and the outer wall 202 of the base trough 201 as illustrated in FIG. 5(a). This will occur if the optical fiber is loaded into the base trough in an organized fashion where the optical fiber does not overlap itself and the distal end of the optical fiber is located below all other optical fibers of the coil. When dispensing, the optical fiber will revolve in the base trough, with the negative angle 205 keeping the distal tip in the corner, away from the exit port. Should the optical fiber not be loaded properly, or the distal end of the optical fiber be relocated during shipping and handling and no longer be located below the other optical fibers of the coil the optical fiber may be pushed to the lid trough 301 by the exiting optical fiber. In this case, the end of the optical fiber will track in the corner created by the top 303 and the outer wall 302 of the lid trough 301 as illustrated in FIG. 5(b). The negative angle 305 will keep the distal tip away from the exit port.

As the surgical fiber is dispensed, it will generally pull to the middle, and may get caught in any seam between the base 200 and the lid 300. This is more likely to occur with small core optical fibers. A seam presents a possible "pinch point" to the optical fiber and once caught in the seam the optical fiber will not dispense. Ideally, the inner wall 204 of the base trough 201 should be angled in order to direct the optical fiber away from any seems between the lid and the base as is the case with the outer wall. This is of more importance to the inner wall as the increased force required to rotate the entire optical fiber coil will reflect on the inner wall. Note that the force on the outer wall is only a result of the optical fiber itself pressing against the side as it tries to lay straight. Due to limitations of the vacuum molding process it is not possible to manufacture the desired angle of the inner wall of the trough. Specifically, two negative angles creating a wedge shaped trough could cause issues with or prevent the material from being appropriately released from the mold. Thus an additional circular trough, the inner lid trough 306, is created in the lid, effectively creating desirable angles in the base and the lid to facilitate the vacuum molding process and create the desired angles for the inner wall to help guide the surgical fiber while being dispensed, and intending to keep the optical fiber towards the bottom 203 of the base trough. In order to reduce or effectively eliminate exposure of the seam between the base and the lid to the optical fiber, the inner lid trough 306 does not match the full height of the base trough 201, thus a space 403 is created between the inner lid trough and the bottom of the base trough. With this configuration, it is generally not possible for the optical fiber to come in contact with the seam 404 created on the inner wall when the lid is mated to the base.

Figure 4D:
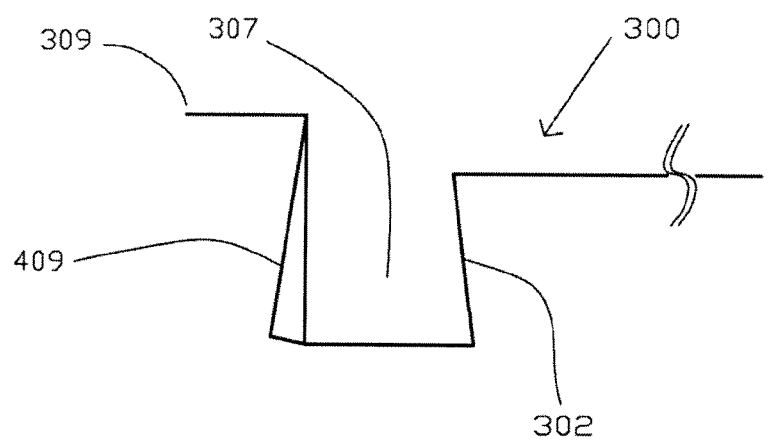
FIG. 4d shows a cross sectional view of a tab.
Figure 4E:
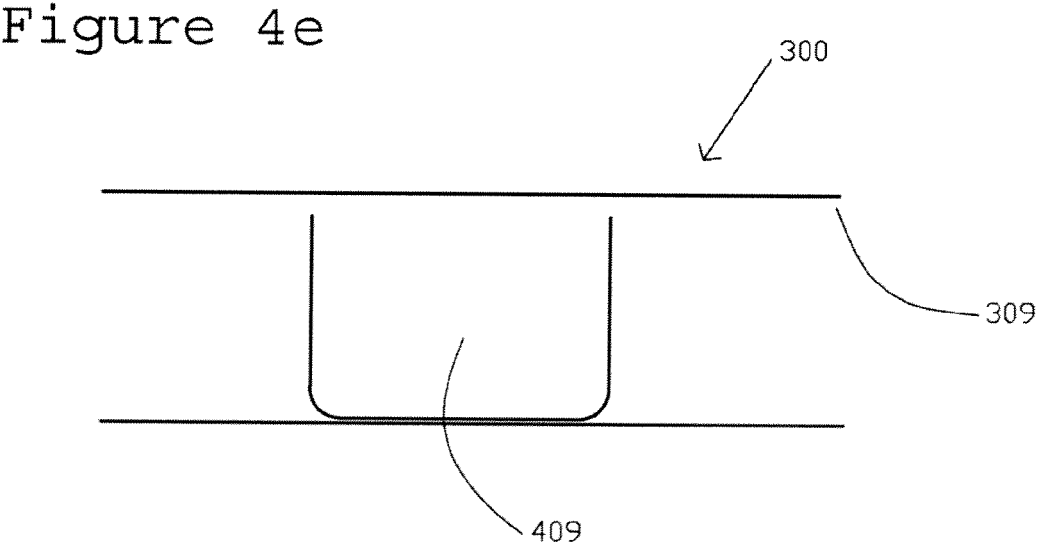
FIG. 4e shows a side view of a tab.

As noted above, the base 200 and lid 300 are press-fit together. There are a number of press fit elements that assist with securing the lid 300 to the base 200 in this manner. For example, in this embodiment, a second circular trough is provided near the outer diameter of the lid. This outer lid trough 307 has a matching groove 206 in the base. The base slot diameter is slightly smaller than the outer lid trough diameter creating a press fit, using the entire circumference of the lid to hold the lid to the base. Alternatively or in addition, to further aid in securing the outer lid trough 307 the base additional tabs 409 may be included as illustrated in FIGS. 4(d)-(e). These tabs may consist of outward distortions in the outer lid trough with matching outward distortions in the base groove 206. Once fitted together the tabs will help to lock the base and lid together. These tabs can be evenly distributed around the perimeter of the lid in for example 6 equally spaced locations. Additional means may be implemented to help hold the lid to the base under adverse conditions such as twisting and or vibration by those skilled in the art. Also, mating dimples (sometimes referred to as "buttons") are provided in the center of the packaging system 100 to further hold the lid to the base. These dimples consist of round dimples 308 in the lid press fitting into square dimples 207 in the base.

Figure 6A:
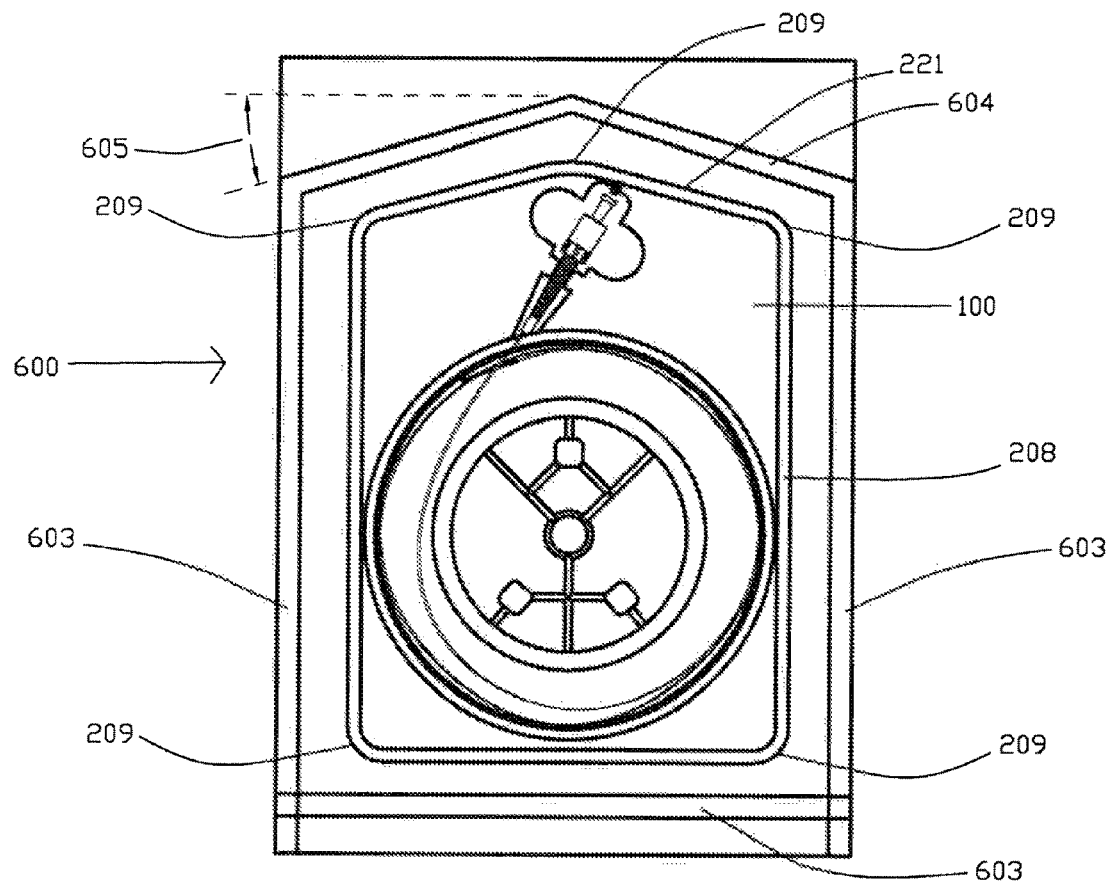
FIG. 6a shows a top view of the packaging system including a tyvek pouch.
Figure 6B:
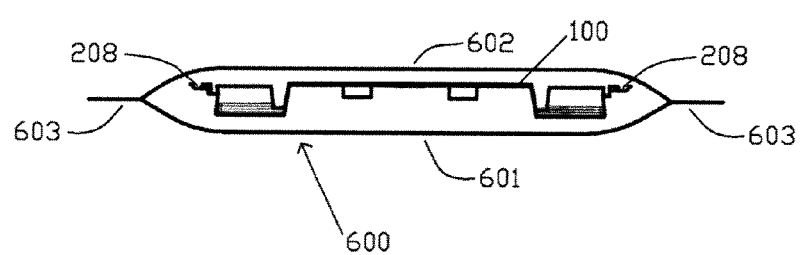
FIG. 6b shows a cross sectional view of the packaging system including the tyvek pouch.

The packaging system 100 is typically loaded into a tyvek pouch as illustrated in FIGS. 6(a)-(b) and shown generally by 600 in order to maintain sterility. The tyvek pouch 600 typically consists of a tyvek layer 601 on one side and a clear plastic polymer layer 602 on the other side, with the sides sealed together. Thus the edge of the packaging system 100 is surrounded on all sides by a seal 603. This seal presents a possible area where the sterile barrier can be compromised if for example a sharp edged object were to press against the seal for a prolonged period of time and with vibration as encountered during shipping. As the packaging system 100 has a substantial mass, when compared to the tyvek pouch, and the edge can be thin, special provisions were incorporated into the packaging system 100 to minimize this effect. A semicircular ridge, the perimeter trough 208, which is continuous around the perimeter edge of the packaging system 100, effectively increases the thickness of the edge of the packaging system 100, minimizing the packaging system 100 effect on the seal.

The perimeter trough 208 also aids to add rigidity to the packaging system 100, helping to keep it flat and prevent twisting.

The shape of the packaging system 100 is designed to generally match the shape of the tyvek pouch, which is typically a rectangle with a chevron seal 604 at one end. The angle of the chevron is typically 15 degrees 605. Maintaining the same shape as the tyvek pouch will help to protect the seal of the tyvek pouch during transit, as a matched shape will spread any forces the packaging system 100 exerts on the pouch seals over the largest possible area. Thus the packaging system may include a chevron 221. The corners of the packaging system 100 are rounded 209 as sharp corners would more easily penetrate the seal of the tyvek pouch during transit. The rounded corners are also beneficial to end users in order to help prevent damage to gloves while handling the packaging system.

Figure 7:
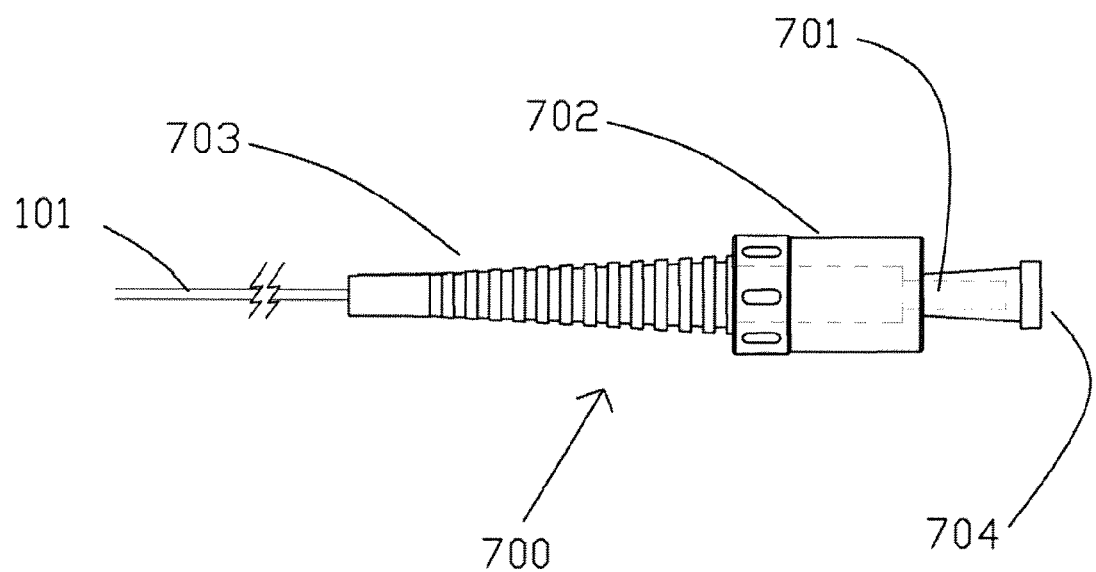
FIG. 7 shows a connector.

Surgical fibers are typically supplied with a connector as illustrated in FIG. 7 and shown generally by 700 in order to connect the optical fiber 101 to the laser system. The connectors typically include a ferrule 701, which is attached to the optical fiber and provides a means of precision mechanical alignment to the laser system. The ferrule typically has a nut 702 attached to it used to secure the ferrule to the laser. The nuts typically can vary in size and shape with features to allow ease of handling. Ferrules also typically house a strain relief 703, a pliable tapered tubing which protects the optical fiber when exiting the connector. The end of the optical fiber and tip of the ferrule, is typically protected with a removable dust cap 704.

The packaging system 100 incorporates a connector well 210 matching the shape of the connector 700 in order to store the connector during shipping and handling. The connector well 210 is typically provided in one of the base or the lid. Built into the well are grippers 211 which apply pressure to the connector to hold it in place, providing sufficient force to hold the connector in place during transit but allow the connector to be easily removed by the user. In the present embodiment, the grippers are positioned to grip the pliable strain relief 703. A number of alternate arrangements are possible and generally known to those skilled in the art.

In order to allow the user to easily grip and remove the connector 700 from the packaging system 100, and thus the optical fiber 101, finger wells 212 are integrated into the packaging system 100. In the current embodiment, the wells are located on either side of the nut 702 of the connector 700.

The surgical fiber is stored in the packaging system 100 by placing the connector 700 in the connector well 210, passing the fiber through the exit port, and coiling the optical fiber 101 in the base trough 201. The optical fiber coil will generally expand to the outer wall 202 of the trough. The lid is then placed on top of the base such that the lid trough engages with the base trough and the lid and base are press fit together. In some cases, the fiber may be packaged without a connector, in this case, a fiber well or channel, somewhat similar to the connector well, may be provided to engage an end of the fiber and the remainder of the fiber would then be passed through the exit port and coiled in the base trough.

The packaging system 100 allows the surgical fiber 101 and 700 to be dispensed at will in a controlled manner. If desired, the configuration of the packaging system 100 allows for only a portion of the optical fiber 101 to be dispensed. This is useful in the operating room environment where maintaining sterility is critical and given the large numbers of equipment and people located close to the patient the surgical fiber is often difficult to control. Dispensing some of the optical fiber allows the connector to be attached to the laser and the remaining optical fiber to be stored in the packaging system 100 until required for surgery, helping to eliminate the possibility of contaminating the sterile optical fiber, by falling on the floor for example.

The surgical fiber is dispensed by removing the connector 700 from the connector well 210 located in the base 200 and pulling the connector away from the packaging system 100. The remaining optical fiber 101 in the packaging system 100 passes through the exit port 105 and begins to revolve in the base trough 201.

Figure 5C:
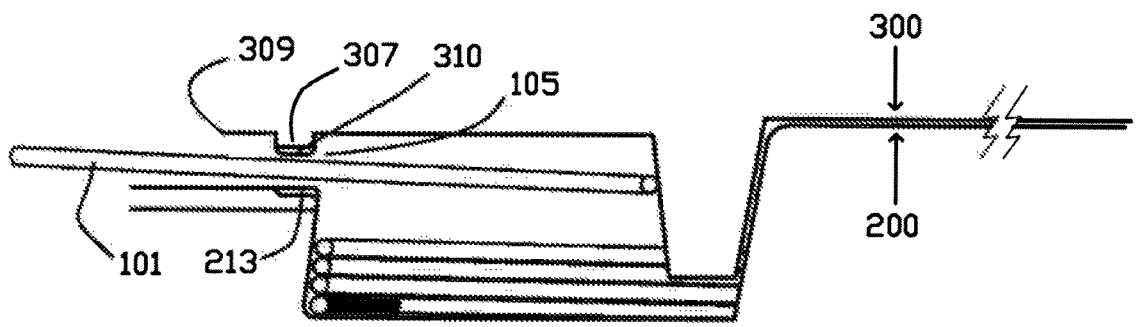
FIG. 5c shows details of the exit port.

Another purpose of the outer lid trough 307 is to provide a smooth surface to the optical fiber 101 while passing though the exit port 105 of the packaging system 100 as illustrated in FIG. 5(*c*). The edge of the lid 309, which is die cut, is relatively sharp, and could damage the optical fiber if it were to scrape on the edge of the lid while being dispensed. The outer lid trough prevents the exiting optical fiber from contacting the edge of the lid by keeping the optical fiber a distance away. Thus the exit port is composed of two smooth surfaces, 213 located in the base and 310 located in the lid.

The exit angle of the exit port 105 is tangent 405 to the inner diameter of the inner wall 304 of the lid trough 301 as illustrated in FIG. 4(*c*). This angle allows the optical fiber to be dispensed more readily, reducing the potential of the distal end of the optical fiber from snagging with the exiting optical fiber which can be the case when the exit angle is tangent to the outer wall 202 of the base trough 201 for example.

The surgical fibers are used for medical applications and must be sterile. Typically the surgical fibers are sterilized by the manufacturer and distributed sterile for first use. The surgical fibers typically come in two forms, single use, where the product is discarded after a single use, and reusable, where the product must be cleaned and re-sterilized prior to each use. After first use, reusable surgical fibers are typically re-sterilized by the end user.

The packaging system 100 must therefore be able to withstand the effects of the sterilization cycle and not inhibit the sterilization of the product. Typical sterilization processes for surgical fibers are Ethylene Oxide (EO) sterilization for first use and steam sterilization for subsequent uses. EO sterilization cycles consist of high vacuum, high humidity and moderate temperatures. Steam sterilization consists of no or moderate vacuum, high humidly and high temperatures. Thus for single use products, low melt point plastics such as HDPE and vinyl are suitable and the design of the packaging system 100 is well suited to vacuum forming. For reusable products a thermo resistant plastic polymer is generally required.

In order to aid the sterilization process, in particular the flow of EO gases, it is important that the product is accessible. If the product were in a fully enclosed container for example, it would be difficult for the gases to reach the product and the product would not be sterile. Also problematic for sterilization are enclosures with only one entrance point as the gases have less ability to flow. Also, as the sterilization process involves a vacuum, it is possible that the plastic polymer 602 material of the tyvek pouch 600 may create a seal on one side of the packaging system 100 blocking access by the gas. Thus it is desirable to supply venting from both sides of the packaging system 100 and in particular the side that will generally face the tyvek as it is porous. Therefore, incorporated into the design of the packaging system 100 are specific venting measures.

The optical fiber 101 is contained in opposing circular troughs 103. The optical fiber exits though the exit port 105, which provides an opening to the trough. By providing additional openings to the trough the optical fiber can be more readily sterilized. Integrated into the packaging system 100 are small grooves, which provide this additional venting into the trough by effectively creating channels.

Venting is provided from the top side of the packaging system 100 by adding small grooves originating from beyond the edge of the lid 309 and extending to the inside of the opposing circular troughs 103. In this case, this vent channel 107 is created by alternating the groove 214 in the base and the groove 311 in the lid. To further ensure venting, the vent is connected to the perimeter trough 208. The perimeter trough is used to link various vents and help ensure EO gases reach the vents. While only one vent is indicated, a number of these vents could be added to the present embodiment. An additional venting channel 215 is provided to link the connector well 210 with the perimeter trough 208 which in turn vents to the opposing circular troughs 103 in the event the plastic polymer material of the tyvek pouch 602 should seal the connector trough 210.

Venting is provided from the bottom side of the packaging system 100 by small grooves embedded in the base. The vents 216 originate from the centre of the packaging system 100 base and extend down the inner wall 204 of the base trough 201. An additional hole 217 is required in the base of the packaging system 100 in order to vent these channels to the bottom side of the packaging system 100. This can be accomplished by the use of a die punch. In order to support the die punching operation and not crimping the ends of the channel, a dimple 218 is provided, with the dimple being pressed while being die cut and then returning to its original shape.

All of the vents are strategically located in order to minimize interaction with the optical fiber, and, in particular, the distal end of the optical fiber, while the optical fiber is being dispensed.

In order to prevent the base 200 and lid 300 from being separated under vacuum, vent grooves are also channeled to each individual press fit dimple 207. Air that is trapped between the base and the lid 406, inside the dimple, could expand under vacuum, causing the lid to push away from the base. Vent grooves 219 are added to the base, originating from the dimple and tying into the vent grooves 216. Additionally, a label 407 can be placed over the dimples on the top side sealing air within the dimple 408. Under vacuum, the air will push on the label, causing distortion of the label or separating the adhesive that holds the label in place. Thus the dimples 308 located in the lid are vented as well. This is accomplished with grooves 312 originating from the dimple in the lid and extending beyond the edge of the label. Corresponding grooves 220 are required in the base in order to accommodate the grooves in the lid. Alternatively the dimples 207 and 308 as well as the label 407 could be vented with a small hole.

Figure 8A:
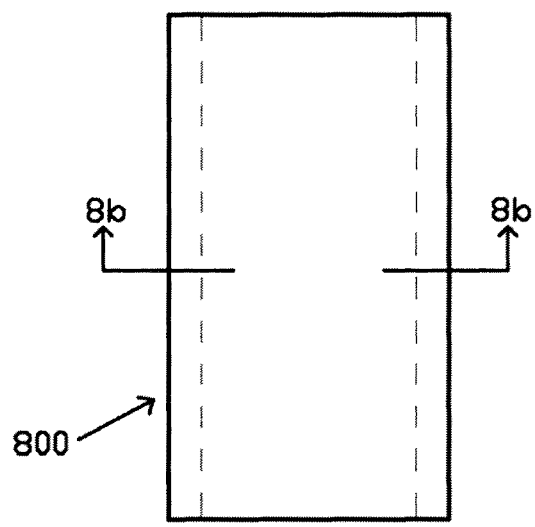
FIG. 8a shows a side view of a tip protector.
Figure 8B:
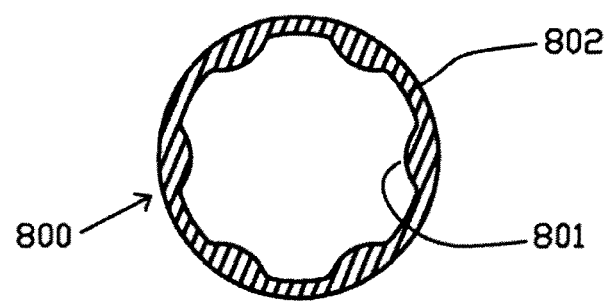
FIG. 8b shows a cross sectional view of the tip protector.
Figure 9A:
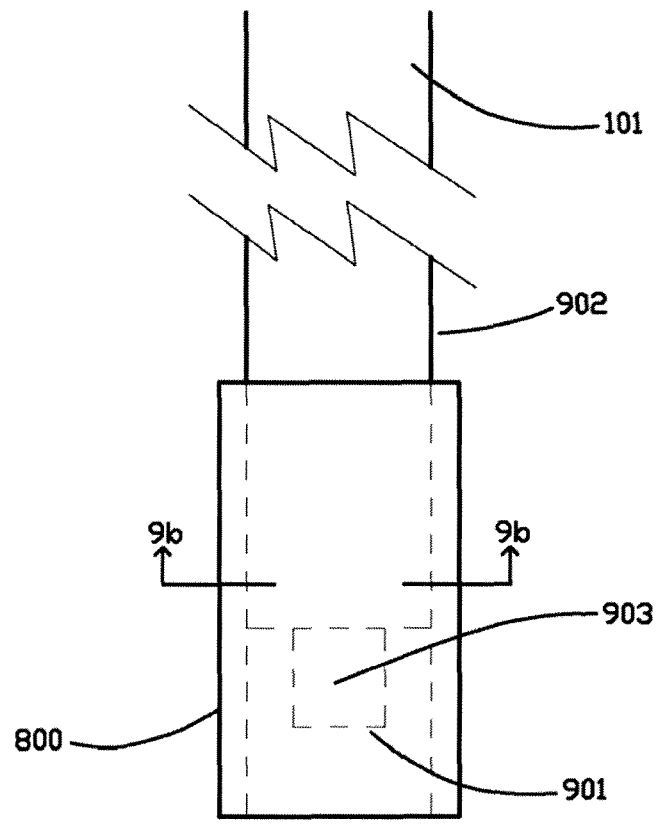
FIG. 9a shows a side view of the distal end of the surgical fiber with tip protector.
Figure 9B:
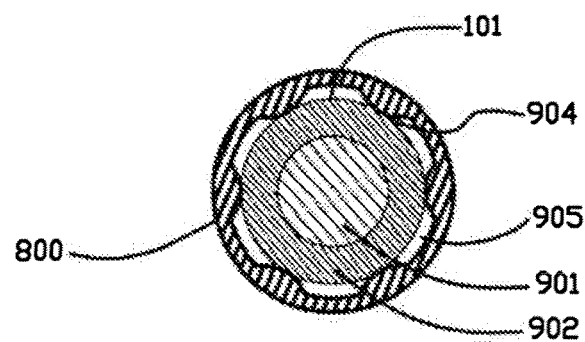
FIG. 9b shows a cross sectional view of the distal end of the surgical fiber with tip protector.

In order to protect the distal end 102 of the optical fiber 101 a tip protector has been developed as illustrated in FIGS. 8(a)-(b) and shown generally by 800. As illustrated in FIGS. 9(a)-(b) the distal end of the optical fiber is cleaved 901 and the jacket 902 is removed, typically in the order of 5 mm. For clarity, the buffer is not shown. Thus the silica glass 903 of the optical fiber is exposed, and the cleaved end face not only creates a very sharp edge but is also easily chipped or damaged. As the optical fiber is dispensed and the distal end travels along the inside of the opposing trough, the sharp edge of the cleaved optical fiber will scrape on the plastic surface and create microscopic particles of plastic which collects on the end face, or the cleaved end could be chipped. This is more pronounced with the large core optical fibers as the force exerted by the optical fiber onto the outer wall of the opposing troughs is far greater. Thus there is a need to protect the cleaved end face of the optical fiber.

The tip protector 800 can be formed as a tube/sleeve of Teflon, or similar lubricious material. The length can be in the range of an inch to a number of inches. The tip protector is configured to grip the optical fiber enough to hold it in place while the optical fiber is being dispensed (travels along the outer wall of the opposing troughs and passes through the exit port) and yet be easily removed by the user prior to use of the surgical fiber. By varying the length of the protector, the amount of grip can be controlled. A longer tip protector will contain more contact surface area and thus provide better grip. In order to help ensure the end user removes the tip protector prior to use, a high visibility color can be selected, such as yellow. Colors commonly used for safety related applications such as yellow, orange and red are desirable.

In order to support EO sterilization, the tip protector tubing should not fully contact the jacket 902 of the optical fiber as this would prevent the EO gas from contacting the encased section of optical fiber. In order to allow the EO gas to penetrate inside the tip protector, the core of the tip protector can be ribbed 801, this reduces the amount of surface contact 904 with the optical fiber 101 and creates channels 905 for the EO gas to enter.

Based on production limitations in the manufacture of optical fibers, the outer diameters of the optical fiber will generally vary in diameter, typically plus or minus 5%. The tip protector should preferably have the ability to grip a range of diameters for each optical fiber size. The ribbed design allows the tip protector to expand, by way of thin wall 802 areas between the grooves, which by way of deforming the outer diameter (which may no longer be perfectly round) thus accommodating the variance in optical fiber diameter.

To further aid in accommodating a range of optical fiber diameters due to tolerance variations, the tip protector 800 can be extruded in a non round shape, such as an oval. This is intended to provide increased grip strength for an optical fiber which is smaller while also providing the ability to accommodate an optical fiber which is larger, becoming round as the optical fibers outer diameter increases.

The tip protector 800 can also be useful in preventing the distal end of the optical fiber becoming caught in any seams between the base and lid of the packaging system 100. By increasing the effective diameter of the optical fiber, the tip protector is less likely to press into a seam and get caught while dispensing. It will be understood that this is of more importance with small core optical fibers.

The tip protector 800 can also be used to help protect the surgical fiber when being inserted into an endoscope. By extending the length of the tip protector from a few inches to a length similar to the length of the endoscope (in the order of a meter) the optical fiber will have an additional layer of protection by providing a barrier between the optical fiber and the inside of the endoscope. Particularly problematic is the area where the optical fiber enters the endoscope. This is of particular importance for small core optical fibers which are more fragile than large core fibers. Since the design of the tip protector supports EO sterilization, it can be supplied to the end user already installed on the surgical fiber. In this application the tip protector may be formed of a lubricious material, such as Teflon, and/or be of a larger diameter such that the tip protector will have the ability to slide over the surface of the optical fiber such that the user can relocate the tip protector away from the distal end of the optical fiber or remove it from the inside of the endoscope all together.

The above-described embodiments are intended to be examples only. Alterations, modifications and variations can be effected to the particular embodiments by those of skill in the art without departing from the scope of the invention, which is defined solely by the claims appended hereto.

We claim:

1. A medical fiber packaging system comprising:
a top portion comprising a top trough, wherein the top trough comprises a top outer side wall, a top inner side wall and a top wall and forms an annular shape on the top portion;
a bottom portion comprising a bottom trough, wherein the bottom trough comprises a bottom outer side wall, a bottom inner side wall and a bottom wall and forms an annular shape on the bottom portion, wherein the bottom trough is configured to engage with the top trough to form an annular area for supporting a medical optical fiber coiled inside the annular area with an end of the optical fiber inside the annular area and wherein the bottom outer side wall is configured to bias the end of the optical fiber towards the bottom wall;
a fastening mechanism to maintain the top portion and bottom portion in a fixed position relative to one another; and
a single port provided to the fiber packaging system configured to support the other end of the optical fiber and to allow the optical fiber to be dispensed from the annular area in a lengthwise fashion.

2. The system of claim 1 wherein the top portion and bottom portion are configured such that the fiber is substantially fully encased.

3. The system of claim 1 wherein the annular top and bottom troughs are substantially circular in shape.

4. The system of claim 1 wherein at least one of the top portion and bottom portion further comprises a connector well external to the annular area to receive a connector provided to an end of the fiber.

5. The system of claim 4 wherein the connector well comprises grips to hold the connector at a strain relief location of the connector.

6. The system of claim 1 wherein the fastening mechanism comprises press fitting the top portion and the bottom portion together.

7. The system of claim 6 wherein the press fitting comprises interlocking press fit elements provided to the top portion and the bottom portion independent from the top trough and bottom trough.

8. The system of claim 7 wherein the system further comprises vents configured to provide access to the interior of the press fit elements from the external environment in order to prevent pressure differentials between the press fit elements.

9. The system of claim 1 wherein the system further comprises vents configured to provide access to the interior of the annular area from the external environment in order to allow the optical fiber to be sterilized.

10. The system of claim 1 wherein the bottom outer side wall is configured to bias an end of the optical fiber towards the bottom wall by forming the bottom outer side wall at an angle in relation to the single port such that a connection between the bottom side wall and the bottom wall is not in the plane of the single port.

11. The system of claim 1 wherein the top outer side wall and the bottom outer side wall top and bottom trough have the same diameter and meet to form a seam and the top outer side wall and the bottom outer side wall are not parallel with a plane of the seam or a plane perpendicular to the seam.

12. The system of claim 11, wherein the single port is provided in either the top outer side wall or the bottom outer side wall adjacent the seam.

13. The system of claim 1 wherein the top inner side wall comprises a top inner trough protruding downwardly into the annular area and configured to protrude past a seam created by the mating of the top portion with the bottom portion but does not extend to the bottom wall.

14. The system of claim 1 wherein the port is arranged tangent to the diameter of the top inner side wall of the annular area.

15. The system of claim 1, wherein the top trough further comprises an outer top trough configured to align with a groove provided in the bottom trough.

16. The system of claim 15 wherein the single port comprises a three sided trough wherein the three sided trough is a section of the outer top trough and is configured to isolate the fiber from sharp edges associated with an outer edge of the top trough as the fiber exits the annular area.

17. The system of claim 1, wherein the system is sealed within a pouch to maintain sterility.

18. The system of claim 1, wherein the top outer side wall is configured to direct the inner end of the optical fiber toward the top wall of the top trough if the optical fiber contacts the top outer side wall when the optical fiber is rotating in the annular area as it is pulled out the single port.

19. The system of claim 1, wherein the single port is provided between the top portion and the bottom portion.

20. The system of claim 1 wherein the top inner side wall extends into the annular area adjacent the bottom inner side wall a distance that is less than the distance to the bottom wall.

21. The system of claim 1 wherein the top portion and the bottom portion are configured to be separable so that the packaging can be reused.

* * * * *